US008676510B2

(12) United States Patent
Watanabe et al.

(10) Patent No.: US 8,676,510 B2
(45) Date of Patent: Mar. 18, 2014

(54) CLINICAL-RESULT CONFIRMING DEVICE, CLINICAL-RESULT CONFIRMING METHOD, AND COMPUTER PROGRAM THEREFOR

(75) Inventors: Tatsuhisa Watanabe, Kanagawa (JP); Hiromi Kataoka, Kochi (JP); Akira Horimoto, Kanagawa (JP)

(73) Assignees: A&T Corporation, Fujisawa-shi (JP); Kochi University, Kochi-shi (JP)

( * ) Notice: Subject to any disclaimer, the term of this patent is extended or adjusted under 35 U.S.C. 154(b) by 1658 days.

(21) Appl. No.: 10/564,083

(22) PCT Filed: Jul. 16, 2004

(86) PCT No.: PCT/JP2004/010520
§ 371 (c)(1),
(2), (4) Date: Jan. 11, 2006

(87) PCT Pub. No.: WO2005/008254
PCT Pub. Date: Jan. 27, 2005

(65) Prior Publication Data
US 2006/0190195 A1    Aug. 24, 2006

(30) Foreign Application Priority Data
Jul. 18, 2003 (JP) ................... 2003-199077

(51) Int. Cl.
*G01N 33/48*    (2006.01)
*G01N 31/00*    (2006.01)
*G06G 7/48*    (2006.01)
*G06G 7/58*    (2006.01)

(52) U.S. Cl.
USPC ............. 702/19; 702/22; 703/11; 703/12

(58) Field of Classification Search
CPC ............. A61B 3/1015; H04N 1/00002; G06K 7/10722; G03H 1/22
See application file for complete search history.

(56) References Cited

U.S. PATENT DOCUMENTS

2004/0073098 A1*    4/2004    Geva et al. ............ 600/300
2004/0161851 A1    8/2004    Horimoto et al.

FOREIGN PATENT DOCUMENTS

| EP | 0389992 | * 3/1990 | ............ G06F 15/80 |
| JP | 2828609 | 9/1998 | |
| JP | 2003-114231 | 4/2003 | |

OTHER PUBLICATIONS

Kataoka et al. (Medical Informatics, 2002, 22(Suppl.), 209-210).*
H. Ioki, et al.; "Clustering of Leukocyte scattergram in allergic diseases;" *Japan Association of Medical Information*; Nov. 14, 2002; pp. 211-212, English Abstract and Supplemental Information (4 Sheets total.)/Discussed in the specification.
H. Kataoka, et al.; "A Similarity Wave Data Search Based on Dynamic Programming—SOM;" *Transactions of Information Processing Society of Japan*; vol. 42; No. SIG. 10; Sep. 15, 2001; pp. 92-99 and Cover Sheet (9 Sheets total.), English abstract is included.

(Continued)

*Primary Examiner* — Larry D Riggs, II
(74) *Attorney, Agent, or Firm* — Kratz, Quintos & Hanson, LLP (57) ABSTRACT

A pattern matching unit performs pattern matching on present data obtained this time in clinical examination of a part of a subject and previous data obtained last time in the clinical examination of the part with reference patterns. Reference patterns that are most closely approximate to the present data and the previous data are selected. A distance calculator calculates a distance between selected reference patterns. A determining unit determines whether a re-examination is necessary based on the distance.

17 Claims, 7 Drawing Sheets (56) References Cited

OTHER PUBLICATIONS

H. Kataoka, et al.; "A Data Mining System for Protein Electrophoresis Waveforms;" *Japanese Journal of Clinical Laboratory Automation*; vol. 26; No. 3; Jun. 1, 2001; pp. 170-175, English abstract in included.

M. Chiba, et al. "Shutsugen Jisseki Zone-ho ni yoru Kensa Kekka Kensho;" *Japanese Journal of Clinical Laboratory Automation*; vol. 25; No. 4; Apr. 1, 1997; pp. 388-390, Cover Sheet and Supplemental Information (5 Sheets total.)

M. Chiba, et al.; "Shutsugen Jisseki Zone-ho ni yoru quality control;" *Rinsho Kensa, Igaku-Shoin Ltd.*; vol. 41; No. 4; Apr. 15, 1997; pp. 428-432 and Supplemental Information (6 Sheets total.)

* cited by examiner

CLINICAL-RESULT CONFIRMING DEVICE, CLINICAL-RESULT CONFIRMING METHOD, AND COMPUTER PROGRAM THEREFOR

TECHNICAL FIELD

The present invention relates to a clinical-result confirming device, a clinical-result confirming method, and a computer program for making a computer execute the method, and, more particularly, to a clinical-result confirming device and a clinical-result confirming method that can effectively check values in last examination using waveforms and image data, and a program for making a computer execute the method.

BACKGROUND ART

In a conventional clinical examination, prescribed items of examinations are performed on each specimen (examination sample provided by a subject for an examination) and the condition of the subject is judged based on the results of its analysis. Particularly, automatic analyzing devices that analyze multiple specimens in a short time have been developed recently, and are introduced in places where clinical examination is needed, such as a laboratory in a hospital. The advance of the clinical examination technology has realized highly reliable examinations and a highly reliable judgment of conditions of subjects based on the results of the examinations.

There is a previous-value check method of determining whether an examination has been performed properly for examination data by comparing a present examination result with a previous examination result for the same subject. This previous-value check method determines that the validity of an examination for present examination data is questionable when present examination data takes an extremely low value contrary to the prediction that examination data on a patient, which, for example, has kept holding a high value, will be somewhat a high value also in this time. The previous-value checking is performed on items that can be quantized as numerical values using an automatic analyzing device (Patent Literature 1: Japanese Patent Publication No. 2828609).

The present applicant has issued a patent application for a clinical-result confirming device that acquires the difference between previous data and present data, that performs pattern matching of the difference with a reference pattern, and that executes previous-value checking based on the value having the shortest distance (Patent Literature 2: Japanese Patent Application Laid-Open No. 2003-114231).

There is a report on making a database of blood cell grain size data and performing clustering using a self organizing map (SOM) to classify cases of diseases and patterns (Non-Patent Literature 1: "Clustering of Leukocyte scattergram in allergic diseases" by Hiromi IOKI et. al., Japan Association for Medical Informatics, 22nd Joint Conference on Medical Informatics, Medical Aiding System/General Speech Session: Medical Aiding System (1), November, 2002).

The conventional technique, however, has the following problems. The configuration according to the Patent document 1 is designed for performing previous-value checking only on items that use numerical values. Therefore, previous-value checking cannot be performed using graphical data such as waveform data of protein electrophoresis and image data such as a blood cell grain size distribution chart. The previous-value checking on such examination data depends on visual recognition, and is thus inefficient.

While in the technology disclosed in the Patent Literature 2, the difference between previous data and present data is obtained to perform matching with a reference pattern, the direct meaning of a value of the difference is unclear. Furthermore, since the value of the difference appears in both a positive (+) value and a negative (−) value depending on the magnitudes of the values of the previous data and the present data, the previous-value checking by this method is difficult to be intuitively understood. Moreover, similarly to the case in the technology disclosed in the Patent Literature 1, the technology of the Patent Literature 2 cannot perform previous-value checking using graphical data.

The present invention has been achieved in view of the above problems, and it is an object of the present invention to provide a clinical-result confirming device and a clinical-result confirming method that can execute a previous-value checking on graphical data, and improve the reliability of determination of the previous-value checking, thereby reducing the time and work to be spent on unnecessary re-examinations, and a computer program for making a computer execute the method.

DISCLOSURE OF INVENTION

To solve the above problems and to achieve an object, the present invention is characterized by the following. A clinical-result confirming device that performs previous-value checking to check a validity of present examination data of a specimen used in a clinical examination includes an input unit configured to input previous examination data and present examination data; a reference-pattern-group storage unit configured to pre-store a group of reference patterns classified into a plurality of levels; a pattern matching unit configured to select, from the group of reference patterns, a reference pattern best matching with the previous examination data, and selects, from the group of reference patterns, a reference pattern best matching with the present examination data; a distance calculating unit configured to calculate a distance between the reference pattern that is placed in the group of reference patterns and that is matching with the previous examination data, and the reference pattern that is matching with the present examination data; and a determining unit configured to compare the distance calculated by the distance calculating unit with a predetermined threshold, and to determine a validity in the previous-value checking based on whether the distance exceeds the threshold.

According to the present invention, previous-value checking using graphical data is possible, thereby enabling efficient determination that has conventionally depended on visual recognition. Moreover, when the present data differs greatly from the previous data merely in values, if the distance between the reference patterns is small, the data can be determined as normal. Thus, the reliability of previous-value checking is improved.

BEST MODE(S) FOR CARRYING OUT THE INVENTION

Exemplary embodiments of the present invention will be explained in detail with reference to the accompanying drawings. An example of a clinical-result confirming device that is connected to an automatic analyzing device in a hospital is explained herein.

Figure 1:
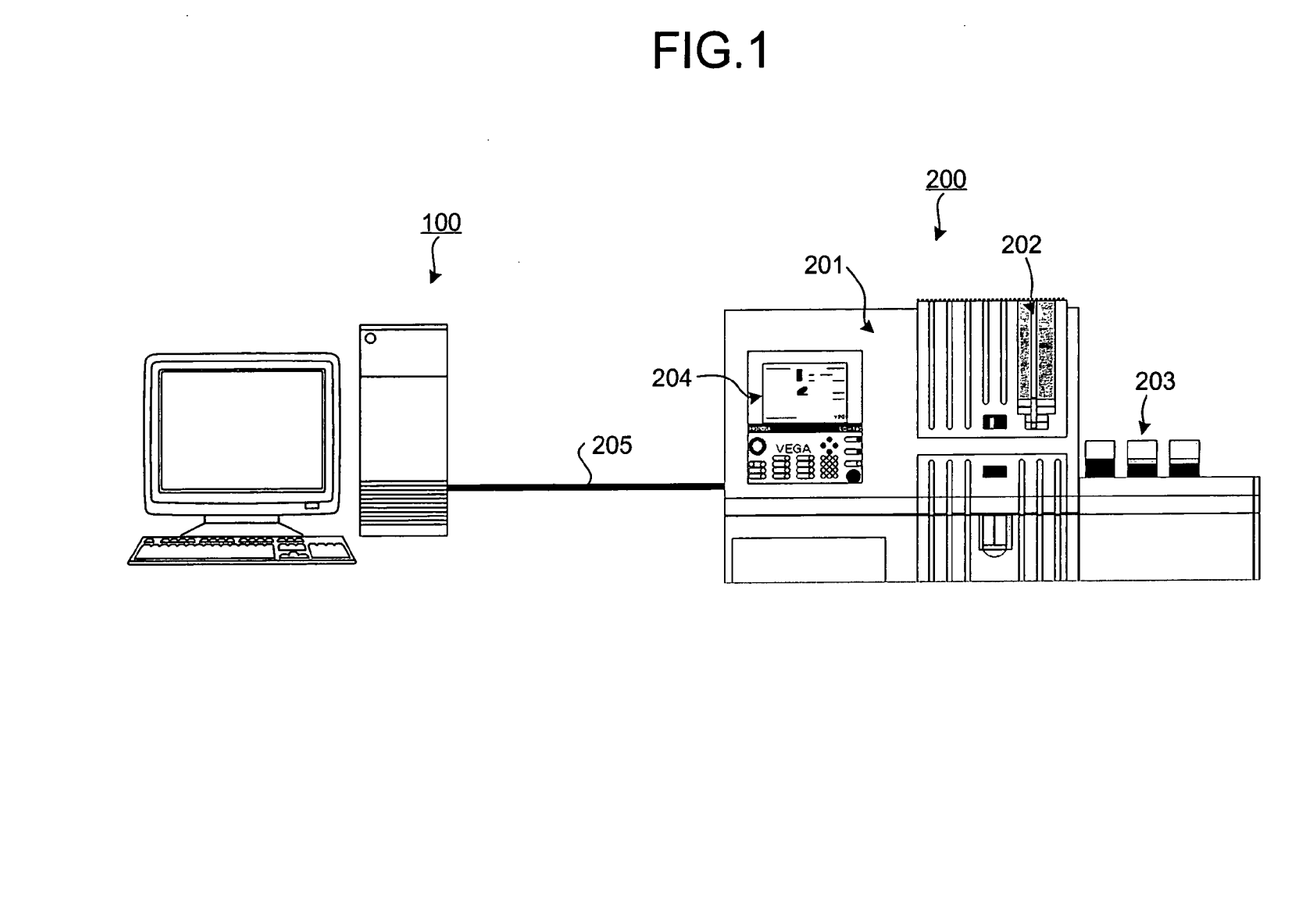
FIG. 1 is one example of an external configuration of a clinical-result confirming device according to the present invention that is connected to an automatic analyzing device.

FIG. 1 is one example of an external configuration of a clinical-result confirming device according to the present invention that is connected to an automatic analyzing device. The clinical-result confirming device 100 receives the results of analysis of clinical examinations of multiple subjects that are output from an automatic blood-cell counter 200, and performs previous-value checking thereon. The clinical-result confirming device 100 determines whether re-examination is necessary through the previous-value checking. The automatic blood-cell counter 200 carries out a clinical examination on specimens of multiple subjects, and sends the analysis results to the clinical-result confirming device 100.

A term "clinical examination" mainly represents a specimen examination that includes a plurality of analysis items for which examinations are performed on the specimen obtained from a subject. The specimen examination may be classified according to the insurance points. The specimen examination includes, for example, a qualitative semi-quantitative urinalysis on general components, a qualitative quantitative urinalysis on specific components, a microscopic urinary sediment examination, a fecal examination, a centesis/collected fluid examination, a blood morphological/functional examination, a hemorrhage/coagulation examination, a blood chemical examination, an endocrinological examination, a tumor marker, a special analysis, an immunohematological examination, an infectious disease serum reaction, a hepatitis virus related examination, an autoantibody examination, a plasma protein immunological examination, a cell function examination, a microscopic bacterial examination of excretion, exudation, or secretion, a bacterial culture identification examination, a bacteria and drug sensitivity examination, an acid-fast bacteria separation and culture-examination, an acid-fast bacteria identification examination, an acid-fast bacteria and drug sensitivity examination, a microorganism nucleic acid identification and quantitative examination, and an animal examination. Each clinical examination includes plural analysis items. The analysis items include, for example, measurement of Na concentration in electrolyte, and refer to plural examination items or analysis items that are included in a clinical examination.

The automatic blood-cell counter 200 will be explained briefly, and then, how the counting result is output will be explained. The automatic blood-cell counter 200, as shown in FIG. 1, includes a counter 201, a consumables storage unit 202, a specimen storage unit 203, a displaying/analyzing unit 204, and a communication line 205 for transferring analysis results to the clinical-result confirming device 100.

Although the detailed description is not given, a blood set in the specimen storage unit 203 is automatically stirred, and is automatically diluted according to a dilution ratio prescribed by the counter 201, and the counter 201 measures the individual items, and outputs the results. The interior of the counter 201 is cleaned for every measurement so that a previous specimen does not mix into a specimen at the time of next measurement. The consumables storage unit 202 stores various kinds of consumables to be counted and measured. The consumables include reagents and cleaning solutions for various counting and measurements.

Figure 5:
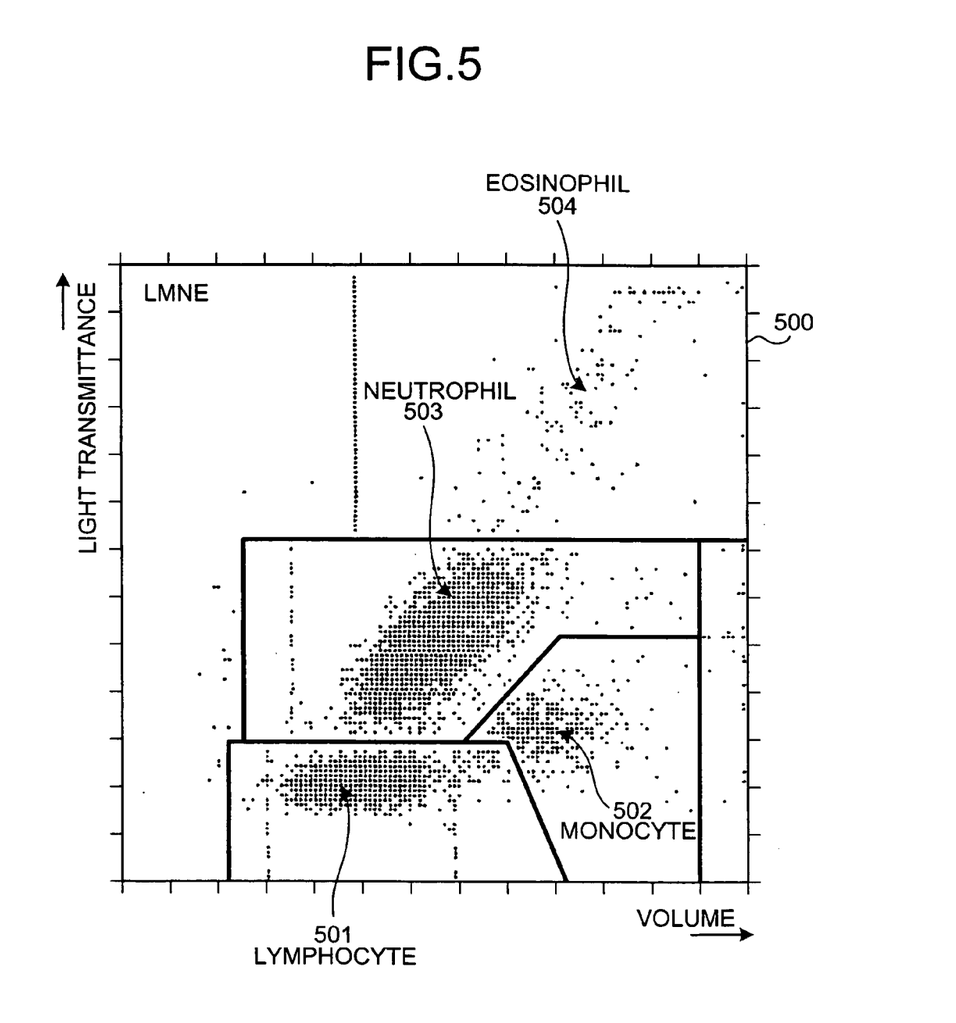
FIG. 5 is an explanatory diagram of an enlarged reference pattern of one among reference patterns shown in FIG. 4.

The displaying/analyzing unit 204 organizes and displays measured items based on measurement results acquired by the counter 201, as necessary. For example, the displaying/analyzing unit 204 prepares a size distribution chart for blood cells using the measured data, or carries out two-dimensional or higher-order population analysis using blood cell characteristics measured simultaneously on two or more items, to perform counting for each group of cells. The displaying/analyzing unit 204 outputs the measurement results from the counter 201 as two-dimensional image data, as shown in FIG. 5 to be discussed later.

The displaying/analyzing unit 204 outputs and displays various kinds of information. The display items include examination items, the date of measurement, the number of specimens, and the progression status of the examination. When an error (failure) occurs during measurement, the content of the error, the device status, and operational procedures for recovery are also displayed. When the validity is questionable in the previous-value checking, a screen prompting re-examination of specimens is displayed, as will be described later.

The communication line 205 transfers a plurality of analysis results of a clinical examination (analysis results output from the counter 201 or the displaying/analyzing unit 204) to the clinical-result confirming device 100. There are various ways of transferring the analysis results, such as network connection though a LAN, a telephone line, USB connection, or the like. However, the transfer mode is not particularly limited as long as the analysis results are quickly output to the clinical-result confirming device 100. As will be described later, data is transmitted through a LAN in this embodiment.

The automatic blood-cell counter 200 outputs analysis results on plural items of multiple subjects each time the analysis results are obtained. As the automatic blood-cell counter 200 is sited in a hospital, the population is a group of persons that have some kind of disorders, and often include multiple items whose values deviate from the values of healthy people. Therefore, it is meaningless to simply perform a re-examination when analysis results take abnormal values, and it is necessary to grasp the tendency of the abnormal values, and determine whether the abnormal values are of values certainly requiring re-examination after determining that the previous-value checking is performed properly.

According to this embodiment, a database of blood cell size data output from the displaying/analyzing unit 204 of the automatic blood-cell counter 200 is made, and object data such as blood cell size images are clustered using the self organizing map (SOM) to provide clustered patterns (blood cell size distribution patterns) that are used in the analysis. Specifically, clustered patterns are used as described in the Non-Patent Literature 1.

Figure 2:
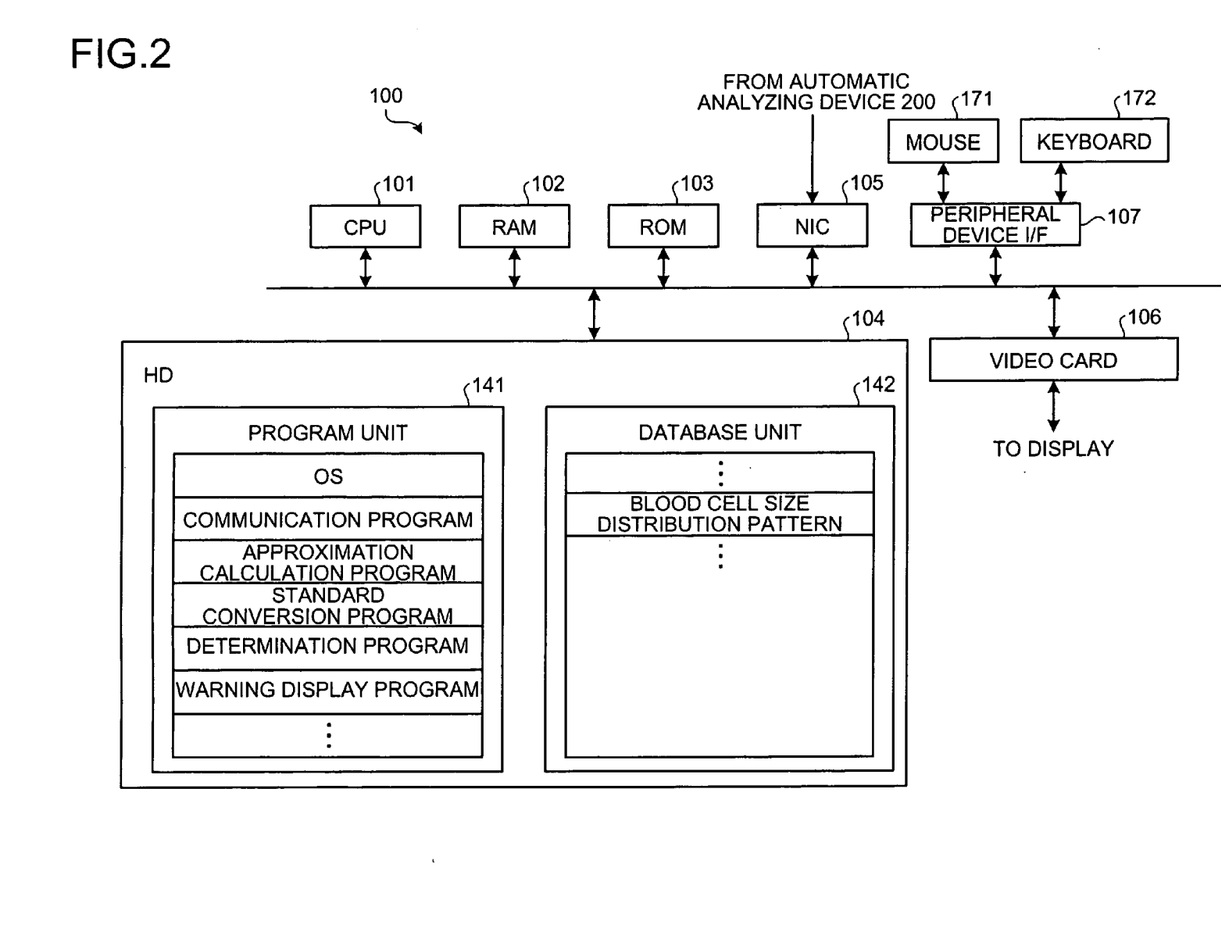
FIG. 2 is an explanatory diagram of one example of a hardware configuration of a clinical-result confirming device 100.

The configuration of the clinical-result confirming device 100 will be explained below. FIG. 2 is an explanatory diagram of one example of a hardware configuration of the clinical-result confirming device 100. The clinical-result confirming device 100 includes, as its hardware configuration, a CPU 101, a RAM 102, a ROM 103, a hard disk (HD) 104, a network interface card (MC) 105, a video card 106, and a peripheral device interface (I/F) 107. To the peripheral device I/F 107, a mouse 171 and a keyboard 172 are connected. A display (see FIG. 1), such as a CRT and an LCD, is connected to the video card 106.

The HD 104 includes a program unit 141 and a database unit 142. The program unit 141 stores an OS that is a program for executing the general basic control of the clinical-result confirming device 100, a communication program, an approximation calculation program, a standard conversion program, a determination program, a warning display program, and the like that are discussed later. Reference patterns (patterns including the blood cell size distribution patterns) corresponding to the types of clinical examinations are stored in the database unit 142 in advance.

Figure 3:
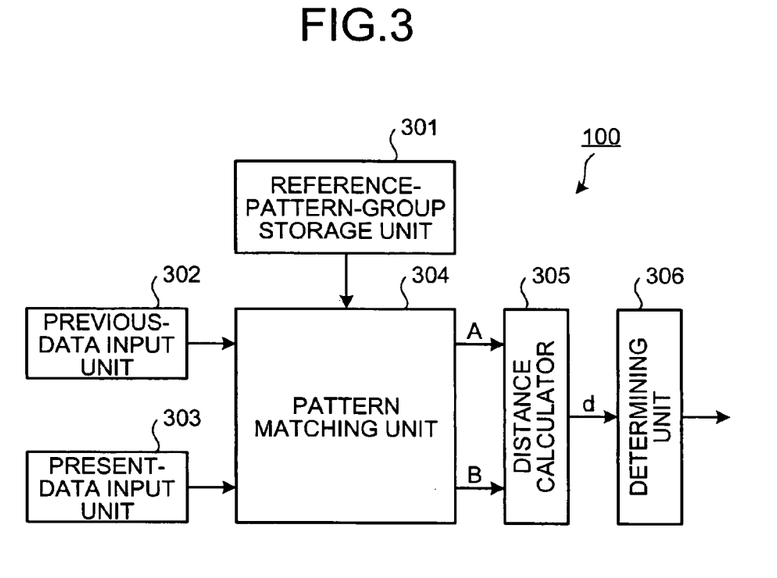
FIG. 3 is an explanatory diagram of one example of a functional configuration of the clinical-result confirming device 100.

The functional configuration of the clinical-result confirming device 100 will be described next, with the explanation of the specific relationship between each functional unit and the hardware shown in FIG. 2. FIG. 3 is an explanatory diagram of one example of the functional configuration of the clinical-result confirming device 100. The clinical-result confirming device 100 includes a reference-pattern-group storage unit 301, a previous-data input unit 302, a present-data input unit 303, a pattern matching unit 304, a distance calculator 305, and a determining unit 306, as the functional configuration.

Figure 4:
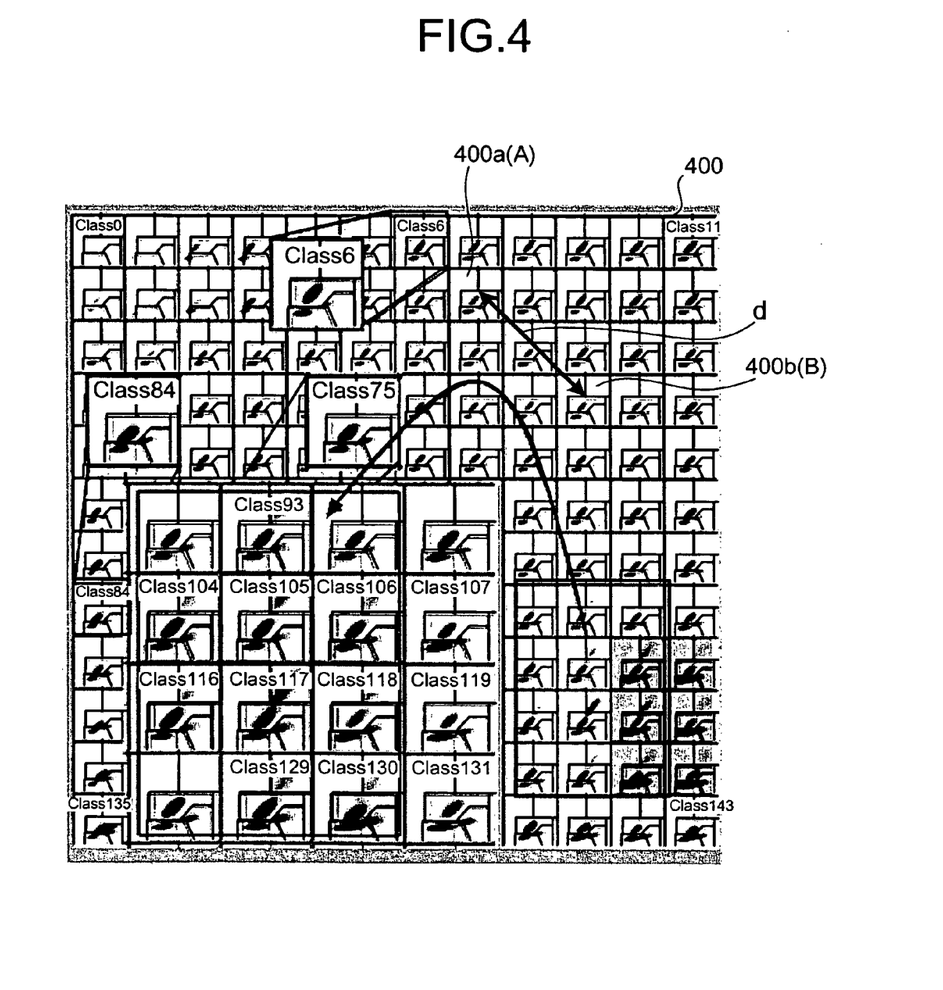
FIG. 4 is a schematic for illustrating a self organizing map where blood cell grain size data is generated by scattergrams.

The reference-pattern-group storage unit 301 stores plural reference pattern groups for performing an analysis. For different analysis items, different reference pattern groups are used. In this embodiment, blood cell size distribution patterns are used as the reference pattern groups. FIG. 4 is a schematic for illustrating a self organizing map where blood cell grain size data is generated by scattergrams. FIG. 4 depicts a group of reference patterns 400 of a competitive layer 144 (12×12, an input layer of 128×128×8 bits). Some reference patterns are displayed in enlargement for the conveniences' sake. FIG. 5 is an explanatory diagram of an enlarged reference pattern of one among reference patterns shown in FIG. 4.

The horizontal axis in FIG. 5 represents the volume of blood cells, and the vertical axis represents the light transmittance. After blood cells are stained, the volume of the blood cells is measured by an electric resistance method, and the cell composition is analyzed by the light transmittance corresponding to the degree of staining. The combination of the two measuring principles, the volume and the light transmittance, allows four types of quantization (lymphocyte 501, monocyte 502, neutrophil 503, and eosinophil 504) to be carried out. The analysis results of counting the specimens are acquired as the same image data as that of a reference pattern 500 shown in FIG. 5.

The reference pattern will be described in detail below. The reference pattern group 400 shown in FIG. 4 is acquired by using the self organizing map (SOM) in the technology described in the Non-Patent Literature 1 using data of the blood examination on multiple (e.g., about 6,000) subjects. The self organizing map is regarded as an efficient method for visualizing latent useful knowledge in data of non-linear multivariable quantities, and helps grasping the correlation among individual items when analysis results (non-linear multivariable quantities) over multiple items are output as in the automatic blood-cell counter 200. As the SOM is one kind of so-called data mining, various schemes, such as mechanical learning and neural network, besides the SOM can be used as long as reference patterns that ensure computation of the order of approximation can be acquired using data mining. The use of the data mining scheme enables determination of correlation of values that are conventionally difficult unless doctors are skilled.

While the total of 144 (=12×12) patterns are shown in the reference pattern group 400 shown in FIG. 4, the quantity is arbitrary and is adequately determined by the number of items or the like of the number of pieces of data of the population (the number of subjects). The reference pattern group 400 includes a two-dimensional matrix of graphical image data, and the patterns like the neutrophil, eosinophil, lymphocyte, and monocyte comprehensively clustered. The reference-pattern-group storage unit 301 can achieve its function with, for example, the database unit 142 in the HD 104 (see FIG. 2).

The individual constituent elements shown in FIG. 3 will be explained next. Previous data acquired in the previous examination of a subject is input to the previous-data input unit 302 from the automatic blood-cell counter 200, and present data acquired in the present examination for the same subject is input to the present-data input unit 303. Suppose that previous data and present data are both image data (see FIG. 5) after analyzing a blood examination on the same examination items. The functions of the previous-data input unit 302 and the present-data input unit 303 can be achieved by, for example, the NIC 105 (see FIG. 2), the CPU 101, and the communication program stored in the program unit 141 in the HD 104.

The pattern matching unit 304 matches reference patterns stored in the reference-pattern-group storage unit 301 with the pattern of the previous data input to the previous-data input unit 302. Likewise, the pattern matching unit 304 matches reference patterns stored in the reference-pattern-group storage unit 301 with the pattern of the present data input to the present-data input unit 303. Specifically, pattern matching is carried out by computing the order of approximation of the reference patterns, and selecting the pattern that has the smallest order of approximation. The method of acquiring degree of approximation is not limited as long as the degree of approximation of the most approximate reference pattern is acquired from among the reference patterns that are subject of comparison.

Figure 6:
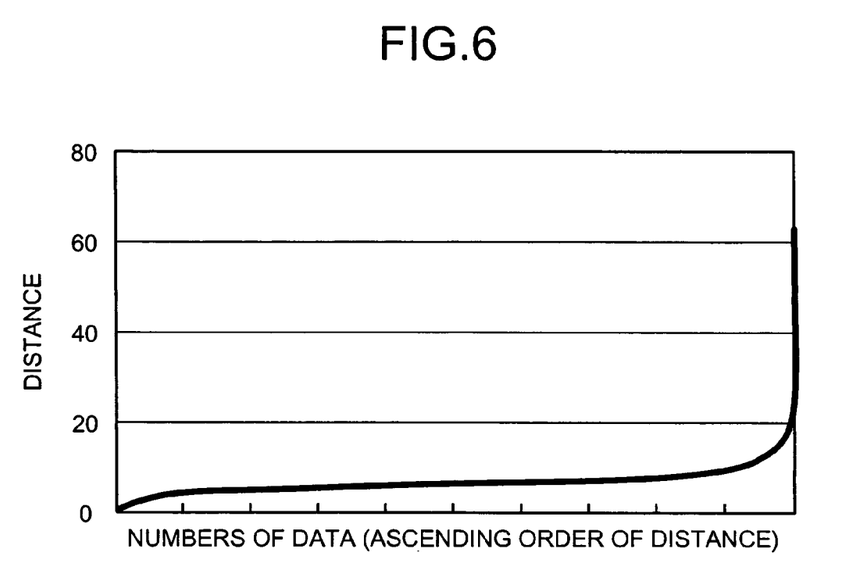
FIG. 6 is an explanatory diagram of distribution of the degree of approximation (shortest distance) of population data used when a reference pattern is acquired based on the reference patterns shown in FIG. 4.

The reference patterns shown in FIG. 4 and the degree of approximation will be explained. FIG. 6 is an explanatory diagram of distribution of the degree of approximation (shortest distance) of population data used when the reference patterns shown in FIG. 4 are acquired. The horizontal axis in FIG. 6 represents the numbers of data, and the vertical axis represents the shortest distance. With regard to the horizontal axis, the numbers are sorted from the left in the ascending order of the distance. As shown in FIG. 6, most subjects have small values in the shortest distance, and do not thus need a re-examination or a thorough examination. On the contrary, at the right end of FIG. 6, the graph rises drastically, having a very large value in the shortest distance. Therefore, the data at the right end is determined as data to be subjected to a re-examination or a thorough examination.

The function of the pattern matching unit 304 can be achieved by, for example, the CPU 101 and the approximation calculation program stored in the program unit 141 of the HD 104.

The distance calculator 305 calculates a distance d between a reference pattern A (400a in FIG. 4) approximate to the present data and a reference pattern B (400b in FIG. 4) approximate to present data that are selected by the pattern matching unit 304. The distance d is the distance in the reference pattern group 400 on the self organizing map. Alternatively, the distances d between each of the reference patterns in the reference pattern group 400 may be calculated or defined to arrange in a list, so that the distance between selected reference patterns A and B is read from the list.

The determining unit 306 performs previous-value checking by comparing the distance d calculated by the distance calculator 305 with a predetermined threshold to determine the validity of the previous data. When the distance d is greater than the threshold, a result of the previous-value checking is determined as NG (the validity of present data is questionable), whereas when the distance d is smaller than the threshold, a result of the previous-value checking is determined as OK (the present data is valid). When determined as NG, the determining unit 306 displays a warning that the result of the previous-value checking is NG (the validity of the present data is questionable) on the display.

The most probable reason for the determination as NG is that a subject or a specimen is mixed up. For example, a specimen can be mixed up due to application of a wrong label (barcode) for identifying a specimen. The use of the clinical-result confirming device 100 according to the present invention can prevent simple medical mistakes. When determined as NG, a warning may be displayed to require a re-examination using the same specimen. When determined as NG, there may be a case in which the measurement and adjustment of the automatic blood-cell counter 200 may be needed. This OK/NG determination is associated with the validity of the present data, and does not determine whether the value of examination data itself is normal or abnormal.

The function of the determining unit 306 can be achieved by, for example, the CPU 101, the determination program and the warning display program stored in the program unit 141 of the HD 104, and the threshold for determination stored in the database unit 142. The threshold can be arbitrarily determined depending on the disease and the contents of an examination.

Figure 7:
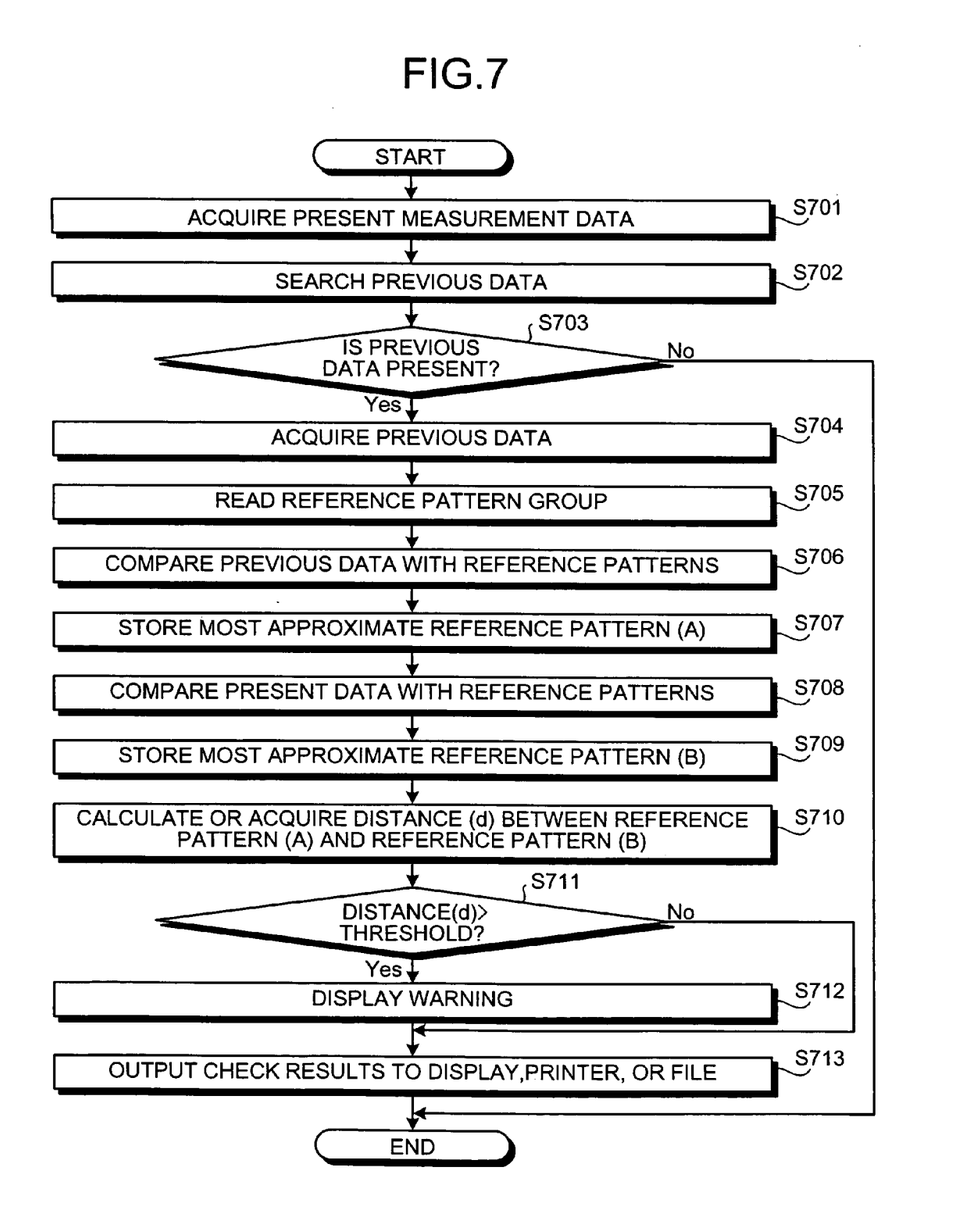
FIG. 7 is a flowchart of procedures for previous-value checking by the clinical-result confirming device 100.

An operational example of the clinical-result confirming device 100 will be explained with reference to a flowchart. FIG. 7 is a flowchart of procedures for the previous-value checking by the clinical-result confirming device 100.

First, an operator (e.g., a laboratory technician) designates a blood cell size distribution as a clinical examination. According to the designation, a corresponding reference pattern and the threshold for determination are read from the database unit 142, and are stored in the RAM 102. The communication program, the approximation calculation program, the standard conversion program, and the determination program are read from the program unit 141, and are stored into the RAM 102 and the cache in the CPU 101. This makes the CPU 101 ready for the operation, so that the CPU 101 acquires present measurement data of the subject from the automatic blood-cell counter 200 according to the communication program (step S701).

Previous data of the same subject is searched next (step S702). If no previous data is found as a result of searching ("NO" at step S703), previous-value checking cannot be carried out, and the process is terminated. If there is previous data ("YES" at step S703), corresponding previous data is acquired (step S704). The reference pattern group 400 (see FIG. 4) of this blood cell size distribution is read out (step S705).

The previous data is then subjected to data conversion by the standard conversion program as necessary, and is compared with all the reference patterns in the reference pattern group 400 (step S706). The approximation calculation program calculates the order of approximation for the reference patterns with respect to the previous data at this pattern collation step, and selects and stores the most approximate reference pattern A (step S707).

Likewise, the present data is subjected to data conversion by the standard conversion program as necessary, and is compared with all the reference patterns in the reference pattern group 400 (step S708). The approximation calculation program calculates the order of approximation for the reference patterns with respect to the present data at the pattern comparison step, and selects and stores the most approximate reference pattern B (step S709).

It is assumed that the previous data and the present data are both output from the automatic blood-cell counter 200 in a form of image data of which format is the same as that of the reference patterns. However, it is not thus limited, and the previous data and the present data may be input in a form of numerical values to the clinical-result confirming device 100 and be converted into image data of the same format as that of the reference patterns. In this case, data conversion by the standard conversion program generates this image data.

The distance d between the selected reference patterns A and B is calculated next (step S710). As mentioned above, the distance d can also be acquired from a list. Acquired distance d is compared with a predetermined threshold (step S711). When the distance d is greater than the threshold ("YES" at step S711), which means that a result of the previous-value checking is determined as NG (the validity of the present data is questionable), a warning is displayed (step S712), and the results of the previous-value checking are output (step S713) and the process is terminated. The output destination is not limited to the display, and print-out from a printer and outputting data to a specific file are also feasible. When the distance d is smaller than the threshold ("NO" at step S711), no warning is displayed at step S712, and the results of the previous-value checking are output (step S713), and the process is terminated.

The clinical-result confirming device 100 executes previous-value checking based on probable patterns, as explained above, thus, it becomes possible to determine whether re-examination of a specimen is really necessary with ease. Although an example of a clinical examination on a subject that is hospitalized or an ambulatory patient or the like is explained, it is not thus limited and a clinical examination can be performed on healthy population. One of applications is a clinical examination to be performed according to a regional difference or an age group.

The clinical-result confirming device 100 can accept a vast amount of clinical examination data input from the automatic blood-cell counter 200. Therefore, plural pieces of clinical examination data may be stored in the HD 104 so that the reference pattern group 400 is reconstructed using the SOM as necessary. The reference pattern group 400 can be constructed by using appropriate software. The reference pattern group 400 is not limited to image data, and may be waveform data.

Specifically, although image data of the blood cell size distribution is used in the embodiment, pattern matching can be carried out by preparing reference patterns of waveform data of protein electrophoresis. The pattern matching using the waveform data can measure the degree of matching based on how waveforms overlie each other, and can be carried out more easily than the pattern matching using image data. When waveform data is used, a group of reference waveform data should be constructed by data mining of the SOM and the like similarly to the case of image data.

As explained above, the clinical-result confirming device according to this embodiment selects patterns that match with previous data and with present data using the reference pattern group 400, and executes previous-value checking based on the distance between the selected reference patterns A and B. It is therefore determined as normal when the distance between the selected reference patterns A and B is small even if the difference between the previous data and the present data is large in numerical values. This can improve the reliability of previous-value checking, thus eliminating unnecessary works and time that are otherwise required in previous-value checking, so that medical expenses can be suppressed.

As the previous data and the present data are both matched with the reference pattern group 400 such as the blood cell size distribution patterns, it is possible to easily and visually confirm the classification of reference patterns and the association of the reference patterns with a predicted case of disease. Changes in the predicted case of disease and examination results can be determined appropriately based on a selection area for the reference patterns in the reference pattern group 400 that are matched with the previous data and the present data, and the frequency of selection in the selection area.

The reference patterns that are matched with the previous data and the present data can be easily selected base on the order of approximation. It is also possible to execute previous-value checking in an examination using the blood cell size distribution that is graphical image data, and previous-value checking in an examination using the protein electrophoresis that is graphical waveform data. It is also possible to execute previous-value checking on graphical data using a group of reference patterns constructed by data mining. Moreover, the display output realizes proper execution of a re-examination on a specimen. Furthermore, previous-value checking for different examinations can be executed by merely reading a necessary reference pattern group from the database. Sequential calculation of distances is not required, and distances of all combinations can easily be acquired by merely reading distances stored in advance.

According to the present invention, as explained above, previous data and present data are not directly compared with each other, and instead, their most matching reference patterns are compared with each other so that previous-value checking using graphical data is possible, thereby ensuring efficient determination that has conventionally depended on visual recognition. Moreover, when the present data differs greatly from the previous data merely in values, if the distance between the reference patterns is small, the data can be determined as normal. Thus, the reliability of previous-value checking is improved.

INDUSTRIAL APPLICABILITY

The present invention is suitable for a clinical-result confirming device that can effectively perform previous-value checking using waveform data and image data.

The invention claimed is:

1. A device for confirming a validity of result of clinical examination of a part of a subject for a clinical examination, the device comprising:
    a computer including:
    a receiving, unit configured to receive a pattern of present data for a subject that is clinical data of a part obtained this clinical examination and a pattern of previous data for the subject that is clinical data of the part obtained last clinical examination;
    a storing unit configured to store a plurality of reference patterns, the reference patterns being classified into a plurality of levels and being arranged two-dimensionally;
    a selecting unit configured to select, from the plurality of reference patterns, a first reference pattern best matching with the pattern of present data and a second reference pattern best matching with the pattern of previous data;
    a calculating unit configured to calculate a value, the value being indicative of a distance between a position of the first reference pattern and a position of the second reference pattern in the plurality of reference patterns arranged two-dimensionally; and
    a determining unit configured to determine a validity of the present data for the subject based on the value, by comparing the value to a predetermined threshold value.

2. The device according to claim 1, wherein the first reference pattern and the second reference pattern are reference patterns most closely approximate to the present data and the previous data respectively.

3. The device according to claim 1, wherein data in each of the present data, the previous data, and the reference patterns includes image data.

4. The device according to claim 1, wherein data in each of the present data, the previous data, and the reference patterns includes waveform data.

5. The device according to claim 1, further comprising a clustering unit configured to perform clustering on the reference patterns.

6. The device according to claim 1, further comprising a display unit configured to display a message indicating that the clinical examination of the part can be wrong when the determining unit determines that the present data is invalid.

7. The device according to claim 1, wherein
    the storing unit includes a database of reference patterns each having reference patterns for a different kind of clinical examination, and
    a group of reference patterns corresponding to the kind of clinical examination being carried out is retrieved from the database to be used.

8. The device according to claim 1, further comprising a value storing unit configured to store a list of values indicative of distances between the first reference pattern and the second reference pattern, wherein
    the calculating unit is configured to extract a value corresponding to the distance between the first reference pattern and the second reference pattern from the list.

9. A method of confirming a validity of result of clinical examination of a part of a subject for a clinical examination, the method comprising:
    receiving a pattern of present data for a subject that is clinical data of a part obtained this clinical examination and a pattern of previous data for the subject that is clinical data of the part obtained last clinical examination;
    storing a plurality of reference patterns, the reference patterns being classified into a plurality of levels and being arranged two-dimensionally;
    selecting, from the plurality of reference patterns, a first reference pattern best matching with the pattern of present data and a second reference pattern best matching with the pattern of previous data;
    calculating a value, the value being indicative of a distance between a position of the first reference pattern and a position of the second reference pattern in the plurality of reference patterns arranged two-dimensionally; and
    determining a validity of the present data for the subject based on the value, by comparing the value to a predetermined threshold value, wherein all of the steps of the method are carried out using a microprocessor.

10. The method according to claim 9, wherein the first reference pattern and the second reference pattern are reference patterns most closely approximate to the present data and the previous data respectively.

11. The method according to claim 9, wherein data in each of the present data, the previous data, and the reference patterns includes image data.

12. The method according to claim 9, wherein data in each of the present data, the previous data, and the reference patterns includes waveform data.

13. The method according to claim 9, further comprising clustering the reference patterns.

14. The method according to claim 9, further comprising displaying a message indicating that the clinical examination of the part can be wrong when a determining unit determines that the present data is invalid.

15. The method according to claim 9, wherein
the selecting includes retrieving a group of reference patterns corresponding to the kind of clinical examination being carried out from a database of reference patterns each having reference patterns for a different kind of clinical examination.

16. The method according to claim 9, further comprising storing a list of values indicative of distances between the first reference pattern and the second reference pattern, wherein
the calculating includes extracting a value corresponding to the distance between the first reference pattern and the second reference pattern from the list.

17. A non-transitory computer-readable recording medium that stores a computer program for making a computer execute:
receiving a pattern of present data for a subject that is clinical data of a part obtained this clinical examination and a pattern of previous data for the subject that is clinical data of the part obtained last clinical examination;
storing a plurality of reference patterns, the reference patterns being classified into a plurality of levels and being arranged two-dimensionally;
selecting, from the plurality of reference patterns, a first reference pattern best matching with the pattern of present data and a second reference pattern best matching with the pattern of previous data;
calculating a value, the value being indicative of a distance between a position of the first reference pattern and a position of the second reference pattern in the plurality of reference patterns arranged two-dimensionally; and
determining a validity of the present data for the subject based on the value, by comparing the value to a predetermined threshold value.

* * * * *